United States Patent [19]
Waddoups et al.

[11] Patent Number: 5,571,950
[45] Date of Patent: Nov. 5, 1996

[54] METHOD FOR TESTING SOOT-RELATED VISCOSITY INCREASE

[75] Inventors: Malcolm Waddoups, Westfield; Arunas T. Lapinas, Pittstown, both of N.J.

[73] Assignee: Exxon Chemical Patents Inc., Linden, N.J.

[21] Appl. No.: 234,079

[22] Filed: Apr. 28, 1994

[51] Int. Cl.$^6$ .................................................. G01N 33/28
[52] U.S. Cl. ........................................ 73/53.05; 73/61.41
[58] Field of Search ..................... 73/10, 53.05, 53.07, 73/54.01, 64.56, 61.41

[56] References Cited

U.S. PATENT DOCUMENTS

| | | | |
|---|---|---|---|
| 4,794,787 | 1/1989 | Gordon | 73/56 |
| 4,873,004 | 10/1989 | Beverwijk | 252/32.5 |
| 5,089,158 | 2/1992 | Van Kruchten | 252/51.5 |

FOREIGN PATENT DOCUMENTS

| | | |
|---|---|---|
| 426884 A1 | 5/1991 | European Pat. Off. . |
| 1498764 | 6/1969 | Germany . |

OTHER PUBLICATIONS

"Kinetic Approach to Engine Oil. 3. Increase in Viscosity of Diesel Oil Caused by Soot Contamination"; *Ing. Eng. Chem. Prod. Res. Dev.*, vol. 20, No. 3, 1981, pp. 540–544 (S. Yasutomi).

"Mechanisms and Control of Viscosity Increase in Railroad Diesel Engine Lubricants"; *Lubricating Engineering*, vol. 42, No. 6, Jun. 1986, pp. 350–356 (M. R. Logan).

"Some Aspects of Tribological Behavior on Dispersed–phase System"; *Lubricating Engineering*, vol. 44, No. 11, Nov. 1988, pp. 913–921 (K. Yoshida).

PCT Search Report (Sep. 14, 1995).

*Primary Examiner*—Michael Brock
*Attorney, Agent, or Firm*—Estelle C. Bakun

[57] ABSTRACT

A method for testing a sample for soot-related viscosity increase comprising: (a) preparing the sample which comprises a major amount of an oil of lubricating viscosity, (b) measuring the viscosity of the sample (c) preparing a stable sample/paste dispersion of the sample and a carbon black paste, (d) equilibrating the sample/paste dispersion, and (e) measuring the viscosity of the sample/paste dispersion, and a method for predicting physical effects of soot-loading on a sample in a test which measures viscosity increase comprising: (1) measuring viscosity increase for a series of reference fluids in the test, (2) measuring viscosity increase for the series of reference fluids in a method having steps (a) to (e), (3) developing a curve, (4) evaluating the sample using the method having steps (a) to (e), and (5) interpolating a viscometric effect for the sample using the curve.

13 Claims, No Drawings

METHOD FOR TESTING SOOT-RELATED VISCOSITY INCREASE

FIELD OF THE INVENTION

This invention relates to a method for testing soot-related viscosity increase. More particularly, this invention relates to a method for evaluating the ability of a sample or the comparative ability of samples to compensate for soot-related viscosity increase. This invention also relates to a method for predicting the physical effect of soot-loading on a sample tested in standardized engine tests.

BACKGROUND OF THE INVENTION

Soot formation can be a problem in diesel engines since the engine environment promotes soot formation, accumulation, and agglomeration. The degree of soot formation depends on design and operating parameters. Problems result in the engine when the soot particles, which are formed in the combustion chamber, and any adsorbed species aggregate to form larger particles which increase system viscosities. Eventually, an engine oil may become so viscous that it cannot be pumped, resulting in engine failure. In addition, hardware design changes have been made in diesel engines to meet emissions requirements and improve environmental performance. These changes have resulted in more soot being diverted to the crankcase and, therefore, certain newer engines have experienced unacceptable viscosity increase.

Therefore, improved lubricants which perform well in a variety of engine types and varying engine conditions and which have better soot handling capabilities are needed. Accordingly, development of a desired lubricant may require extensive engine tests to determine success. However, the tests used to evaluate how a given lubricant performs, e.g., tests which evaluate soot-related viscosity increase in diesel engines, are very expensive, time consuming, and require a large amount of test sample. In addition, testing may be hindered by test stand availability. Determining crucial parameters for lubricant formulations by matrixing designed experiments, therefore, may be prohibitive.

As a result, there has been a clear need in the industry for a bench test which correlates well with standardized engine tests, for example, the Mack Truck Technical Services Standard Test Procedure No. 5GT 57 entitled "Mack T-7: Diesel Engine Oil Viscosity Evaluation," dated Aug. 31, 1984 ("Mack T-7") and the Mack Truck Technical Services Standard Test Procedure entitled "Mack T-8: Diesel Engine Oil Viscosity Evaluation," dated October 1993 ("Mack T-8"). Several bench test designs have attempted to create simulated soot loading, but published tests have not achieved stable simulated soot loading or successful correlation with standardized engine tests and, at the same time, reproducibility.

One test entailed diluting a used oil and observing the resulting viscosity. The presumption was that a good oil will result in a lower overall viscosity. However, this technique was unsuccessful because of the strong non-Newtonian nature of thickened oils. For example, addition of a fresh oil to a used oil can produce as much as a 20% viscosity decrease which masks any generated viscosity interaction when different fresh oils are tested and also indicates that oil additions just prior to any viscosity measurement will drastically alter results.

Because it was recognized that soot played a role in the thickening of engine oils, bench test development using carbon black was initiated. In one bench test, carbon black was dispersed into fresh engine oils using sonic shear and the viscosity response was measured. This technique was first tested using an ultrasonic bath and then a high power sonicator, e.g., SONICATOR W-375. However, the carbon black in the dispersions would gradually precipitate when left standing in contrast to used oil samples which have the ability to maintain their soot loading in suspension. This method of creating a carbon dispersion by sonic shear does not sufficiently mimic an engine environment.

Direct dispersion, which is another bench test attempt, requires dispersing carbon black directly into a sample. For example, in Chevron's soot-thickening test method LPTL 2007A, a specified amount of carbon black can be blended into an oil and the time for a volume of the oil to flow through a calibrated glass capillary viscometer is measured. In another bench test method, carbon black has been directly dispersed into a sample using a high-speed blender followed by agitation at elevated temperatures. "Fluffy" or low density carbon black was used, although it is awkward to handle, because the fluffy carbon black can be dispersed directly by the high-speed blender. However, these methods appear to be unsuccessful because the direct dispersion systems rapidly precipitated. Consequently, these systems do not accurately simulate soot loading and, therefore, fail to accurately recreate an engine test environment.

This invention seeks to provide a solution to the deficiencies in previous bench test systems by providing a bench test that simulates the physical effects of soot-loading in standardized engine tests and generates results which are reproducible and correlate well with the engine tests. In particular, the bench test method of this invention creates a carbon black agglomerate size which is an order of magnitude smaller than in the previous bench tests using direct dispersions and which is more closely related to the size of soot particles in used oils.

SUMMARY OF THE INVENTION

This invention relates to a method for testing a sample for soot-related viscosity increase. The method comprises: (a) preparing the sample which comprises a major amount of an oil of lubricating viscosity, (b) measuring the viscosity of the sample (c) preparing a stable sample/paste dispersion of the sample and a carbon black paste, (d) equilibrating the sample/paste dispersion, and (e) measuring the viscosity of the sample/paste dispersion.

The stable sample/paste dispersion can be prepared by (i) mixing a high structure, fluffy carbon black with an oil-soluble carrier, which can include 150 solvent neutral base oil or the bulk solvent used in the sample, to form a carbon black mixture, (ii) milling the carbon black mixture to form a carbon black paste, and (iii) combining the carbon black paste with the sample, which can be selected from the group consisting of basestocks and formulated oils, by blending. The blending can be conducted in a Waring blender at about 12,000 to 13,000 rpm for about 1 to 5 minutes. The sample/paste dispersion can then be equilibrated by stirring, which can be conducted on a stirrer for about 5 minutes to 1 hour at a temperature of 60° to 90° C. The sample/paste dispersion can conveniently contain from about 1 to 4 weight % of carbon black.

In another embodiment, a dispersant can be added, before step (ii), to the carbon black mixture which can then be stirred. In addition, shear can be applied after preparing the sample, after measuring the viscosity of the sample, after preparing the sample/paste dispersion, or after equilibrating the sample/paste dispersion in order to mimic the shear effects of an engine environment.

A further embodiment of this invention relates to a method for predicting physical effects of soot-loading on a sample in a test which measures viscosity increase. The method comprises: (1) measuring viscosity increase for a series of reference fluids in the test, (2) measuring viscosity increase for the series of reference fluids in a method having steps (a) to (e) as described above, (3) developing a curve, (4) evaluating the sample using the method having steps (a) to (e), and (5) interpolating a viscometric effect for the sample using the curve. The test measuring viscosity increase for which physical effects of soot loading are being predicted can include the Mack T-8 test. Conveniently, the sample and the series of reference fluids can differ by only one component or a combination of components.

DETAILED DESCRIPTION OF THE INVENTION

In the method for testing a sample for soot-related viscosity, the sample which comprises a major amount of an oil of lubricating viscosity is prepared and then the viscosity of the sample is measured. Generally, viscosity measurements of the sample are made according to standard practices using any conventional viscometer including a reverse flow viscometer. Suitable viscometers include a Sil viscometer, Cannon-Fenske Routine viscometers, Cannon-Fenske Opaque viscometers, and a Zeitfuchs #4 reverse flow viscometer. The sample which comprises a major amount of oil of lubricating viscosity can include, for example, mineral oils, synthetic oils, and fully formulated oils which contain, for example, dispersants, anti-oxidants, and detergents.

Then a stable sample/paste dispersion is prepared from the sample and a carbon black paste. The term "stable" refers to the fact that the carbon black particles do not precipitate out of the sample/paste dispersion over a period of time, typically greater than 4 hours, preferably 24 hours to one week. The sample/paste dispersion is created to mimic the soot-induced viscometric effect of running the sample in an engine test. Typically, 25 to 250 grams of sample are used to prepare the sample/paste dispersion, preferably 25 to 40 grams.

The carbon black paste is prepared by mixing a carbon black with an oil-soluble carrier to form a carbon black/carrier mixture (hereinafter "carbon black mixture") and then comminuting the mixture to form a finely dispersed carbon black paste (hereafter "carbon black paste") with a carbon black agglomerate size of less than about 500 nm, preferably 15 nm to 500 nm, more preferably 15 nm to 200 nm.

Carbon black having a particle size similar to the particle size of soot can be used, e.g., a particle size ranging from about 10 to 80 nm, preferably 20 to 40 nm. Generally, the carbon black can have any structure, i.e., low or high structure. Structure is a property which describes the degree to which the carbon black particles have formed agglomerates. Therefore, high structure carbon blacks contain larger distributions of agglomerates of carbon black particles than low structure carbon black. Oil absorption (dibutyl phthalate) (ASTM #D-2414-70), which is a measure of the amount of fluid to fill the voids between the particles, can be used as a guide to structure level. High structure carbon black generally has an oil absorption value above 100 cc/100 grams, typically 100 to 330 cc/100 grams, and low structure carbon black generally has an oil absorption value of below 70 cc/100 grams, typically 50 to 70 cc/100 grams. Generally, the higher the oil absorption, the higher the structure. The carbon black used to prepare the carbon black paste preferably is high structure since it more closely mimics the actual soot particle distribution in an engine and, thus, more closely reproduces the typical behavior of an engine environment where relatively small mass fractions of soot, e.g., less than 5%, can cause very large viscosity increases, e.g., greater than 50%. The carbon black can be low density carbon black (referred to as "fluffy" carbon black) or high density, i.e., pelleted, carbon black.

Suitable carbon blacks include carbon black made by Cabot Corporation, Boston, Massachusetts, and listed in Cabot's Technical Report S-36. Examples of suitable carbon black includes carbon black having the following ASTM D1765 Classification numbers which are commercially available from Cabot under the trade names shown parenthetically: N110 (Vulcan® 9), N 219 (Regal® 600), N326 (Regal® 300), N472 (Vulcan® XC-72 and its fluffy counterpart Vulcan® XC-72R), N539 (STERLING® SO-1 ), N550 (STERLING® SO), N762 (STERLING® NS-1), and N774 (STERLING® NS).

Preferably, the carbon black is fluffy carbon black, most preferably, a high structure fluffy carbon black, since fluffy carbon black is easier to disperse. If a fluffy carbon black is used, the carbon black can initially be mixed with the oil-soluble carrier with a spatula for about 5 to 30 minutes, preferably 20 to 30 minutes, at a temperature ranging from about 25° to 90°, preferably 25°–35° C.

Any oil-soluble carrier which is soluble in the test sample can be used alone or as mixtures. Suitable oil-soluble carriers include solvent neutral base oils having a solvent neutral number less than 300, preferably 90 to 150, and any bulk solvent used in the test sample. The oil-soluble carrier may cause a small viscosity decrease in the final viscosity measurement but this decrease is offset by the larger viscosity increase associated with the presence of carbon black. The oil-soluble carrier viscosity effect can be monitored by first diluting a test sample with 150 solvent neutral base oil according to the quantity to be contained in the carbon black mixture and calculating the true viscosity increase. However, testing has shown that the extra oil-soluble carrier generally causes an almost constant offset. Therefore, viscosity increases reported herein will neglect the dilution effect.

The carrier can be used in an amount which provides good dispersancy for the carbon black yet avoids changing the characteristics of the sample. A suitable ratio of carbon black to oil-soluble carrier can range from 1:99 to 50:50, preferably 5:95 to 30:70, more preferably 10:90 to 20:80.

Optionally, after forming the carbon black mixture, a dispersant or mixtures of dispersant may be added and stirred to further disperse the carbon black. Suitable dispersants may be selected from any of the well known oil soluble salts, amides, imides, amino-esters, and oxazolines of long chain hydrocarbon substituted mono and dicarboxylic acids or their anhydrides; thiocarboxylate derivatives of long chain hydrocarbons; long chain aliphatic hydrocarbons have a polyamine attached directly thereto; and Mannich condensation products formed by condensing a long chain substituted phenol with formaldehyde and polyalkylene polyamine.

Any dispersion equipment which sufficiently breaks down the agglomerate size of the carbon black and which sufficiently disperses the carbon black agglomerates can be used to form the carbon black paste. Suitable dispersion equipment depends in part on the type of carbon black selected and can include those described in "Dispersion of Carbon Black For Plastics, Inks, Coatings and Other Special Applications," Cabot Technical Report S-31, May 1980, pages 6–15. For example, for fluffy carbon black, three roll mills or colloid mills can be used.

When using a high structure, fluffy carbon black, the carbon black paste is conveniently formed by milling with a three-roll mill which consists of three rolls rotating at different speeds for transfer of material from roll to roll. Material to be dispersed is fed into the nip between the feed and center rolls and the mill base is dragged into the space between these rollers, where part of the material is returned to the feed bank and the other part undergoes high shear as it passes through the feed nip and into the space between the center roll and the apron roll. As the material passes through this space, high shear is again achieved and, as the material emerges, it is again split with part returning to the feed bank and the other part flowing to the take-off apron. The mill rollers are adjusted fairly tightly, e.g., approximately 400 psi, to afford a small particle size result and afford shear to further disperse the carbon black. Approximately 50 grams of carbon black paste at a time are fed onto the rotating rollers. As described above, the carbon black paste is transferred from roller to roller thus dispersing the particles and evacuating air from the mixture. A tray with a knife edge can be affixed to the third roller to remove the milled carbon black paste. At this tight roller tolerance setting, it takes approximately 8 to 10 hours to pass about 1600 grams of carbon black paste through the mill. The three roll mill works well in dispersing fluffy carbon black in systems of high or "paste" consistency.

A standard draw plate grind gauge can be used to determine the initial seed pattern of the carbon black, the scratches representing the larger agglomerate sizes measured on the draw plate. The initial seed pattern depends on the carbon black selected. Maximum agglomerate sizes falling in the range of 5 to 25 µm, preferably 5 to 10 µm, are preferred. Each pass through the three-roll mill decreases the maximum agglomerate size, e.g., approximately 5 µm after one pass and approximately 3 µm after two passes, with a maximum agglomerate size after milling of typically between 1 and 6 µm, preferably 1 to 5 µm.

If a pelleted carbon black is used, the pelleted carbon black can be comminuted using high shear dispersion equipment. Suitable high shear dispersion equipment includes a Banbury mill, ball mill, shot mill, or pebble mill. After comminution, the pelleted carbon black can be combined with an oil-soluble carrier as described above to form a carbon black mixture. Then the carbon black mixture can be dispersed in the dispersion equipment which sufficiently breaks down the agglomerate size of the carbon black and which sufficiently disperses the carbon black agglomerates as described above. If the pelleted carbon black is combined with the oil-soluble carrier prior to comminution in the high shear dispersion equipment, subsequent addition of oil-soluble carrier may not be required if the mixture is already paste-like.

Notably, the presumed quality of the sample plays an important role in determining how many "passes" through the dispersion equipment is required to form the carbon black paste for the bench test. For example, if the sample is thought to have good resistance to soot-related viscosity increase (whether as a basestock or a finished formulation) the viscosity increase is expected to be low and, therefore, only one pass may be desired to form the carbon black paste. If, however, the sample is thought to be a poorer quality oil, two or three passes may be required for the carbon black mixture in order to more vigorously break down the carbon black agglomerates and more thoroughly disperse the carbon black.

After the carbon black paste is prepared, the stable sample/paste dispersion is prepared by blending the carbon black paste into the sample. The blending can be performed by any suitable method sufficient to cause mixing and further dispersion of the carbon black, e.g., using a Waring blender. The choice of blending equipment may determine the amount of sample required. The blending is conducted at a range from about 8,000 rpm to 18,000 rpm, preferably 12,000 to 13,000 rpm and for a period of time ranging from about 1 to 10 minutes, preferably 1 to 5 minutes, most preferably 3 to 5 minutes. After blending, the sample/paste dispersion is equilibrated by stirring on a stirrer for a period of time sufficient to produce a stable sample/paste dispersion and enhance the solid-liquid contacting, conveniently ranging from 5 minutes to 8 hours, preferably 5 minutes to 1 hour, at a temperature of at least 25° C., preferably 25° C. to 90° C., most preferably 60° to 90° C.

Generally, the amount of carbon black dispersed in the sample is less than 10 weight % based on the weight of the sample, preferably 0.005 to 10 weight %, and most preferably 1 to 4 weight %.

Because an engine environment creates a shear effect, for example, by breaking apart viscosity modifiers which may be present in the sample, optionally, shear can be applied during the bench test using external mechanical means to mimic shear effect. Specifically, shear equipment which would have energy levels sufficient to break polymer chains of viscosity modifiers can be used. The required energy level depends on the viscosity modifier present in the sample. The shear can be applied sonically, for example, using a SONICATOR W-375. Alternatively, a Kurt Orbahn device may be used to shear the sample by high velocity flow through a fixed orifice, which may be tuned for the particular viscosity modifier present in the sample. The shear application can occur before or immediately after measuring the viscosity of the sample, after preparing a stable sample/paste dispersion, or after equilibrating the stable sample/paste dispersion.

The sample/paste dispersion is then transferred to a reverse flow viscometer and the viscosity of the sample/paste dispersion is measured. Typical reverse flow viscometers include Cannon-Fenske Opaque viscometers and a Zeitfuchs #4 viscometer. The Zeitfuchs #4 viscometer is preferred. Generally, prior to making the viscometric measurement, the temperature of the sample/paste dispersion is equilibrated for 15 minutes to 100° C. The results are generally reported as the difference in viscosity between the dispersion and the initial sample.

The method for predicting the physical effects of soot-loading on a sample in a test which measures viscosity increase ("engine test") comprises, as a first step, measuring viscosity increase for a series of reference fluids in the engine test. Then, the viscosity increase is measured for this series of reference fluids using the method of this invention ("bench test") described above. A standardized curve can then be developed for the series of reference fluids in the engine test and the series of reference fluids in the bench test. The sample to be tested is then run in the bench test to determine viscosity increase. The viscosity increase value is compared to the values determined for the reference fluids run in the bench test to determine the ranking of the sample.

The relative value can then be interpolated to predict the viscometric effect in the engine test.

The prediction method can also be used to determine the viscometric effect of individual components or a combination of components. Testing individual component responses can include testing from among many candidates for a given type of component, e.g., determining which basestock more positively affects viscosity increase. Samples which differ in regard to only one component, either by concentration or actual molecular structure, may be studied by this bench test method in order to advance understanding of formulation component effects in a given engine test. In addition, testing viscometric effect of a combination of components can be accomplished by testing the utility and/or effects of a component class, e.g., dispersants, rust inhibitors, or antioxidants, by using sets of samples specifically designed to highlight the contribution of each component in each set. In either case, major component effects can be obtained by subtractive blending, e.g., components can be inserted and then eliminated from the test sample to determine the effect on viscosity response. Alternatively, several test samples which differ from each other by only one component or a combination of components can be run against reference fluid(s).

The engine tests can include the Mack T-7 and the Mack T-8 tests, which are part of a panel used to determine acceptability of oils for engines manufactured by Mack Truck Company. In the Mack T-7 test, a direct injection, in-line six cylinder four stroke turbo-charged series charge air-cooled compression ignition engine is operated at a low speed, high torque, steady state condition. The kinematic viscosity of the lubricant is measured after the engine has run 100 hours and at the end of the test at 150 hours. These two points are used to determine a rate of viscosity change ("viscosity slope"). A passing oil will demonstrate a viscosity increase less than or equal to 0.04 cSt/hr.

The Mack T-8 test is more severe than the Mack T-7 test. The Mack T-8 test takes into account the retarding of fuel injection timing in newer engines to allow the engines to pass emission requirements. The Mack T-8 also requires fuels having a lower sulfur content. The retarded fuel injection results in high soot related viscosity increase, high filter pressure drops, and sludge deposits in these newer engines. The test runs at 1800 rpm for 250 hours. Throughout the test, soot levels and viscosity are measured. The measured viscosities and soot levels are used to interpolate a viscosity at a soot level of 3.8 weight %. An oil passes if that viscosity differs from the lowest viscosity measured in the test by 11.5 cSt or less. If two tests are run, the average result must be 12.5 cSt or less. If three tests are run, the average result must be 13.0 cSt or less.

This invention may be further understood from the following examples which are not intended to limit the scope of the claims.

EXAMPLES

I. Correlation With The Mack T-7 Test

A. Three fully formulated oils were prepared and run in the Mack T-7 test. These same oils were then run according to the bench test of this invention by first measuring the viscosity of the oils after allowing the oils to equilibrate for 15 minutes at 100° C. in a Zeitfuchs #4 reverse flow viscometer. Then, a carbon black mixture was obtained by hand mixing Cabot XC-72R carbon black in 150 solvent neutral base oil with a carbon black to base oil weight ratio of 20:80 and milling the carbon black paste in a three-roll mill until a maximum particle size of 2 µm was measured on a draw plate, which required three passes through the mill. 2.4 grams of carbon black paste and 37.6 grams of sample were weighed and placed into a Waring mini-cup blending container and blended for five minutes at 13,000 rpm. The mixture was transferred to a 150 ml beaker and stirred at 70° C. for one hour. The sample/paste dispersion was then charged to a Zeitfuchs #4 reverse flow viscometer and the viscosity was read after the sample/paste dispersion was equilibrated for 15 minutes at 100° C.

Below are the results from the Mack T-7 test and the bench test, reported as viscosity increase in units of cSt as measured at 100° C.

| SAMPLE | Mack T-7 Test[1] (cSt) | Carbon Black[2] Bench Test (cSt) |
|---|---|---|
| 1 | 5.69; 5.17 | 11.19 |
| 2 | 2.17; 2.07 | 7.40 |
| 3 | 1.77 | 1.68 |

[1]The maximum viscosity increase over the 150 hour engine test.
[2]The amount of carbon black loading was 1.2%.

As shown by the data, the rank order for viscosity increase results in the bench test correlates exactly with the Mack T-7 viscosity increase results.

B. Seven fully formulated oils were prepared and run in the Mack T-7 test. These same oils were then run according to the bench test of this invention by first measuring the viscosity of the oils after allowing the oils to equilibrate for 15 minutes at 100° C. in a Zeitfuchs #4 reverse flow viscometer. Then, a carbon black mixture was obtained by hand mixing Cabot XC-72R carbon black in 150 solvent neutral base oil with a carbon black to base oil weight ratio of 20:80 and milling the carbon black paste in a three-roll mill until a maximum particle size of 2 µm was measured on a draw plate, which required three passes through the mill. 2.80 grams of carbon black paste and 37.2 grams of sample were weighed and placed into a Waring mini-cup blending container and blended for five minutes at 13,000 rpm. The mixture was transferred to a 150 ml beaker and stirred at 70° C. for one hour. The sample/paste dispersion was then charged to a Zeitfuchs #4 reverse flow viscometer and the viscosity was read after the sample/paste dispersion was equilibrated for 15 minutes at 100° C.

| SAMPLE | Mack T-7[3] (cSt) | Carbon Black[4] Bench Test (cSt) |
|---|---|---|
| 1 | 3.72 | 13.66 |
| 2 | 1.91 | 8.7 |
| 3 | 2.89 | 9.7 |
| 4 | 1.46 | 4.8 |
| 5 | 1.27 | 2.3 |
| 6 | 0.86 | 2.7 |
| 7 | 0.70 | 1.9 |

[3]Viscosity increase during the last 50 hours of the engine test.
[4]The amount of carbon black loading was 1.4%

The test results indicate that the bench test discriminates between good and bad oils and correlates with the Mack T-7 test.

II. Correlation With The Mack T-8 Test

Seven fully formulated oils were prepared and run in the Mack T-8 test. These same oils were then run according to the bench test of this invention. Specifically, the viscosity of the oils were measured by a Zeitfuchs #4 reverse flow viscometer, after the oils were equilibrated for 15 minutes at 100° C. A carbon black mixture was obtained by handmixing Cabot XC-72R carbon black in 150 solvent neutral base oil with a carbon black to base oil ratio of 20:80, the resulting carbon black paste was further dispersed using a 3-roll mill. The carbon black paste was milled twice giving a maximum particle size of 2.5–3.0 microns. Approximately 3 or 4 grams of the milled carbon black paste and approximately 27 or 36 grams of sample, respectively, to provide a carbon black active ingredient concentration of 2% by weight, were weighed and placed into a Waring blender and blended for 5 minutes at 13,000 rpm. This blended mixture was then further equilibrated by placing it into a 150-ml beaker and stirring at low speed for 1 hour at 70° C. The sample containing 2 weight % finely dispersed carbon black was then charged to the Zeitfuchs #4 reverse-flow viscometer, where it was allowed 15 minutes to equilibrate to 100° C., at which point the viscosity of the sample/paste dispersion was taken.

Below are the results from the Mack T-8 test (reported as viscosity increase at 3.8% soot relative to the lowest measured viscosity during this 250-hr engine test) and the bench test. All viscosity increases are reported in units of cSt as measured at 100° C. and represent the viscosity of the sample/paste dispersion containing finely dispersed carbon black minus the viscosity of the oil.

| Sample | Mack T-8 Engine Test | Carbon Black[5] Bench Test |
|---|---|---|
| 1 | 30.0 | 36.29 |
| 2 | 30.7 | 28.82 |
| 3 | 22.0 | 19.28 |
| 4 | 11.0 | 4.07 |
| 5 | 11.3 | 3.14 |
| 6 | 7.6 | 2.91 |
| 7 | 5.2 | 1.13 |

[5]In Sample Nos. 1, 2, 3, and 4, the amount of carbon black was 4 grams and the amount of sample was 36 grams. In Sample Nos. 5, 6, and 7, the amount of carbon black paste was 3 grams and the amount of sample was 27 grams.

As shown by this data, the rank order of the bench test results correlates well with the Mack T-8 engine test results at 3.8% soot.

III. Individual Component Response

Three fully formulated oils having different basestocks but the same detergent inhibitor package and viscosity modifier were prepared and run in the Mack T-8. These same oils were then run according to the bench test of this invention. Specifically, the viscosity of the oils were measured by a Zeitfuchs #4 reverse flow viscometer, after the oils were equilibrated for 15 minutes at 100° C. A carbon black mixture was obtained by hand-mixing Cabot XC-72R carbon black in 150 solvent neutral base oil with a carbon black to base oil ratio of 20:80, the resulting carbon black paste was further dispersed using a 3-roll mill. The carbon black paste was milled twice giving a maximum particle size of 2.5–3.0 microns. Approximately 3 grams of the milled carbon black paste and approximately 27 grams of sample, respectively, to provide a carbon black active ingredient concentration of 2% by weight, were weighed and placed into a Waring blender and blended for 5 minutes at 13,000 rpm. This blended mixture was then further equilibrated by placing it into a 150-ml beaker and stirring at low speed for 1 hour at 70° C. The sample containing 2 weight % finely dispersed carbon black was then charged to the Zeitfuchs #4 reverse-flow viscometer, where it was allowed 15 minutes to equilibrate to 100° C., at which point the viscosity of the sample/paste dispersion was taken.

Below are the results from the Mack T-8 test (reported as viscosity increase at 3.8% soot relative to the lowest measured viscosity during this 250-hr engine test) and the bench test. All viscosity increases are reported in units of cSt as measured at 100° C. and represent the viscosity of the sample/paste dispersion containing finely dispersed carbon black minus the viscosity of the oil.

| Sample | Mack T-8 Engine Test | Carbon Black Bench Test |
|---|---|---|
| 1 | 7.6 | 2.91 |
| 2 | 5.2 | 1.13 |
| 3 | 4.6 | 1.05 |

As shown by this data, the rank order of the bench test results correlate exactly with the Mack T-8 engine test results. Therefore, the effectiveness of the basestocks used, which were varied in each sample, was determined.

What is claimed is:

1. A method for testing a sample for soot related viscosity increase, the method comprising:
    (a) obtaining a sample which comprises a major amount of an oil of lubricating viscosity,
    (b) measuring the viscosity of the oil;
    (c) preparing a stable sample/paste dispersion of the sample and carbon black paste;
    (d) equilibrating the sample/paste dispersion, and
    (e) measuring the viscosity of the sample paste dispersion, wherein shear is added to mimic the shear effects of an engine environment at any time after said step (a).

2. The method of claim 1, wherein the sample/paste dispersion is prepared by (i) mixing a high structure, fluffy carbon black with an oil-soluble carrier to form a carbon black mixture, (ii) milling the carbon black mixture to form a carbon black paste, and (iii) combining the carbon black paste with the sample by blending.

3. The method of claim 2, wherein the blending is conducted in a Waring blender at about 12,000 to 13,000 rpm for about 1 to 5 minutes.

4. The method of claim 2, wherein the oil-soluble carrier is 150 solvent neutral base oil.

5. The method of claim 2, wherein the carrier is the same as a bulk solvent used in the sample.

6. The method of claim 2, wherein the sample/paste dispersion contains from about 1 to 4 weight % of carbon black, based on the weight of the sample.

7. The method of claim 2, wherein before step (ii) a dispersant is added to the carbon black mixture and the carbon black mixture is stirred.

8. The method of claim 1, wherein the sample/paste dispersion is equilibrated by stirring.

9. The method of claim 8, wherein the stirring is conducted on a stirrer for about 5 minutes to 1 hour at a temperature of 60° to 90° C.

10. The method of claim 1, wherein the sample is selected from the group consisting of basestocks and formulated oils.

11. A method for predicting physical effects of soot-loading on a sample in an engine test which measures viscosity increases comprising:
    (1) measuring viscosity increase for a series of reference fluids in the engine test,
    (2) measuring viscosity increase for [the] said series of reference fluids of step (1) using a method comprising:
        (a) measuring an initial viscosity of each fluid in said series of reference fluids of step (1), (b) preparing a series of stable dispersions each comprising a reference fluid and a carbon black paste, (c) equilibrating said series of stable dispersions, and (d) measuring final viscosities for each stable dispersion and determining viscosity increases by subtracting the initial viscosity from the final viscosity for each stable dispersion, (3) developing a curve of said viscosity increases for said series of reference fluids in said engine test of step (1) as a function of said viscosity increases of said series of reference fluids in the method of step (2), (4) measuring the viscosity increase of the sample using the method of step 2 wherein said sample is used in place of said series of reference fluids, and (5) interpolating a viscometric effect for said sample using said curve of step (3).

12. The method of claim 11, wherein the test is Mack T-8.

13. The method of claim 11, wherein the sample and the series of reference fluids differ by one component or a combination of components.

* * * * *